Figure 1A:
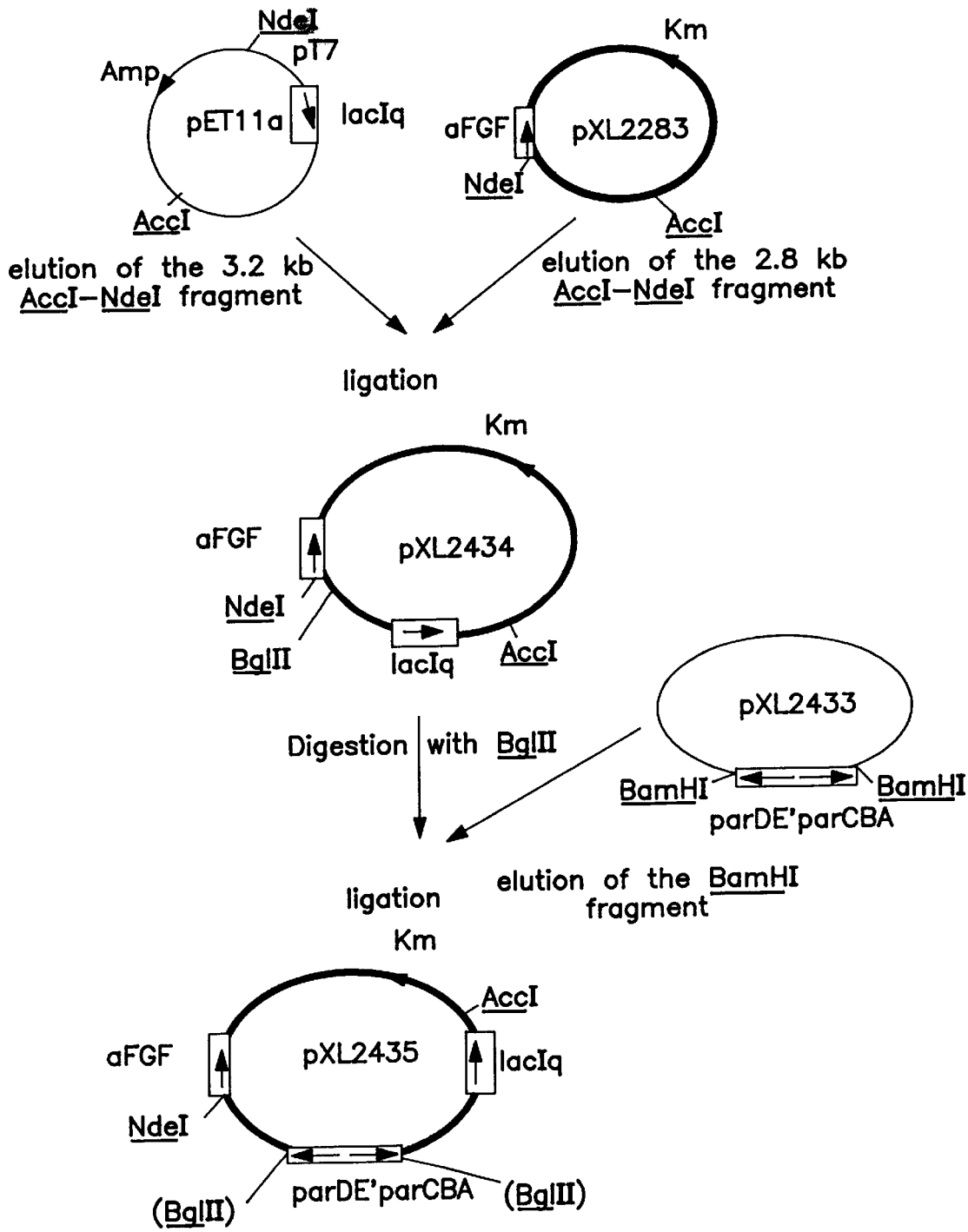

United States Patent [19]
Cameron et al.

[11] Patent Number: 6,143,518
[45] Date of Patent: Nov. 7, 2000

[54] METHOD FOR THE PRODUCTION OF RECOMBINANT PROTEINS, PLASMIDS AND MODIFIED CELLS

[75] Inventors: Béatrice Cameron, Paris; Jöel Crouzet, Sceaux, both of France

[73] Assignee: Rhone-Poulenc Rorer SA, Antony Cedex, France

[21] Appl. No.: 08/793,900

[22] PCT Filed: Sep. 14, 1995

[86] PCT No.: PCT/FR95/01178

§ 371 Date: Mar. 12, 1997

§ 102(e) Date: Mar. 12, 1997

[87] PCT Pub. No.: WO96/08572

PCT Pub. Date: Mar. 21, 1996

[30] Foreign Application Priority Data

Sep. 16, 1994 [FR] France .................................. 94 11049

[51] Int. Cl.$^7$ .................................................. C12N 15/00
[52] U.S. Cl. ................... 435/69.1; 435/320.1; 435/252.3; 435/252.33; 536/23.1; 536/24.1; 536/23.5
[58] Field of Search ................ 435/320.1, 69.1, 435/252.3, 252.33; 536/23.1, 24.1, 23.5

[56] References Cited

FOREIGN PATENT DOCUMENTS

| 0 259 953 | 3/1988 | European Pat. Off. . |
|---|---|---|
| 0 360 006 | 3/1990 | European Pat. Off. . |
| 0 406 738 | 1/1991 | European Pat. Off. . |
| WO 84/01172 | 3/1984 | WIPO . |

OTHER PUBLICATIONS

Gerlitz et al. (1989) Dechema Biotechnol. Conf. vol. 3, No. Pt.A, Jt. Meet. Sim Dechema, Presentation Biochem. Lab., Microb. Princ. Bioprocesses, Appl. Genet., pp. 365–368.
Tabor et al. (1995) Proc. Natl. Acad. Sci USA, 82:1074–1078.
Studier et al. (1990) Methods in Enzymol. 185:60–89.
Gerlitz et al. (1990) J. Bacteriol. 172:6194–6203.
Haigermoser et al. (1993) J. Biotechnol. 28:291–299.
Biard et al. (1992) Biochimica et Biophysica ACTA, 1130:68–74.
Haigermoser et al., Stability of r–microbes: Stabilization of plasmid vectors by the partitioning function of broad–host–range plasmid RP4, J. of Biotechnology, 28, 2,3, p. 291–299 (1993).
Tabor et al., A bacteriophage T7 RNA polymerase/promoter system for controlled exclusive expression of specific genes, Proc. Natl. Acad. Sci., 82, p. 1074–1078, (1995).
Studier et al., Use of T7 RNA Polymerase to Direct Expression of Cloned Genes, Methods in Enzymology, 185, p. 60–89, (1990).
Crouzet et al., Construction of a broad–host–range non–mobilizable stable vector carrying RP4 par–region, Gene, 110, p. 105–108, (1992).

*Primary Examiner*—Robert A. Wax
*Assistant Examiner*—Enrique D. Longton

[57] ABSTRACT

Expression plasmids comprising a nucleic acid sequence of interest controlled by a T7 bacteriophage promoter and a stabilizing region comprising all or part of the par region of the RP4 plasmid or a derivative thereof. The invention also concerns the use of said plasmids in the production of recombinant products.

19 Claims, 3 Drawing Sheets

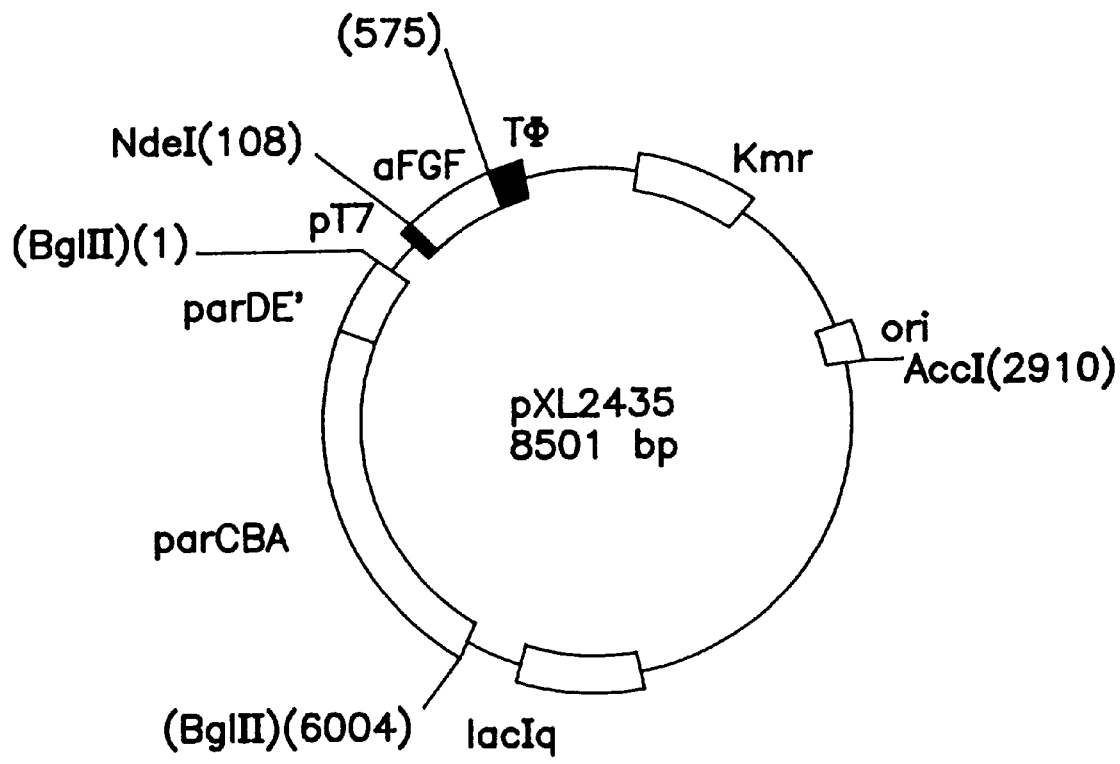
FIG. IB

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
        (A) LENGTH: 8501 base pairs
        (B) TYPE: nucleic acid
        (C) STRANDEDNESS: double
        (D) TOPOLOGY: circular (ii) MOLECULE TYPE: cDNA (xi) SEQUENCE DESCRIPTION: SEQ ID NO:1:

```
GATCTCGATC CCGCGAAATT AATACGACTC ACTATAGGGG AATTGTGAGC GGATAACAAT      60

TCCCCTCTAG AAATAATTTT GTTTAACTTT AAGAAGGAGA TATACATATG GCTGAAGGGG     120

AAATCACCAC CTTCACAGCC CTGACCGAGA AGTTTAATCT GCCTCCAGGG AATTACAAGA     180

AGCCCAAACT CCTCTACTGT AGCAACGGGG GCCACTTCCT GAGGATCCTT CCGGATGGCA     240

CAGTGGATGG GACAAGGGAC AGGAGCGACC AGCACATTCA GCTGCAGCTC AGTGCGGAAA     300

GCGTGGGGGA GGTGTATATA AAGAGTACCG AGACTGGCCA GTACTTGGCC ATGGACACCG     360
```

-continued

```
ACGGGCTTTT ATACGGCTCA CAGACACCAA ATGAGGAATG TTTGTTCCTG GAAAGGCTGG      420
AGGAGAACCA TTACAACACC TATATATCCA AGAAGCATGC AGAGAAGAAT TGGTTTGTTG      480
GCCTCAAGAA GAATGGGAGC TGCAAACGCG GTCCTCGGAC TCACTATGGC CAGAAAGCAA      540
TCTTGTTTCT CCCCCTGCCA GTCTCTTCTG ATTAAAGAGA TCCGGCTGCT AACAAAGCCC      600
GAAAGGAAGC TGAGTTGGCT GCTGCCACCG CTGAGCAATA ACTAGCATAA CCCCTTGGGG      660
CCTCTAAACG GGTCTTGAGG GGTTTTTTGC TGAAAGGAGG AACTATATCC GGATATCCAC      720
AGGACGGGTG TGGTCGCCAT GATCGCGTAG TCGATAGTGG CTCCAAGTAG CGAAGCGAGC      780
AGGACTGGGC GGCGGCCAAA GCGGTCGGAC AGTGCTCCGA GAACGGGTGC GCATAGAAAT      840
TGCATCAACG CATATAGCGC TAGCAGCACG CCATAGTGAC TGGCGATGCT GTCGGAATGG      900
ACGATATCCC GCAAGAGGCC CGGCAGTACC GGCATAACCA AGCCTATGCC TACAGCATCC      960
AGGGTGACGG TGCCGAGGAT GACGATGAGC GCATTGTTAG ATTTCATACA CGGTGCCTGA     1020
CTGCGTTAGC AATTTAACTG TGATAAACTA CCGCATTAAA GCTTATCGAT GATAAGCTGT     1080
CAAACATGAG AATTCTTAGA AAACTCATCG AGCATCAAAT GAAACTGCA  ATTTATTCAT     1140
ATCAGGATTA TCAATACCAT ATTTTTGAAA AAGCCGTTTC TGTAATGAAG GAGAAAACTC     1200
ACCGAGGCAG TTCCATAGGA TGGCAAGATC CTGGTATCGG TCTGCGATTC CGACTCGTCC     1260
AACATCAATA CAACCTATTA ATTTCCCCTC GTCAAAAATA AGGTTATCAA GTGAGAAATC     1320
ACCATGAGTG ACGACTGAAT CCGGTGAGAA TGGCAAAAGC TTATGCATTT CTTTCCAGAC     1380
TTGTTCAACA GGCCAGCCAT TACGCTCGTC ATCAAAATCA CTCGCATCAA CCAAACCGTT     1440
ATTCATTCGT GATTGCGCCT GAGCGAGACG AAATACGCGA TCGCTGTTAA AAGGACAATT     1500
ACAAACAGGA ATCGAATGCA ACCGGCGCAG GAACACTGCC AGCGCATCAA CAATATTTTC     1560
ACCTGAATCA GGATATTCTT CTAATACCTG GAATGCTGTT TTCCCGGGGA TCGCAGTGGT     1620
GAGTAACCAT GCATCATCAG GAGTACGGAT AAAATGCTTG ATGGTCGGAA GAGGCATAAA     1680
TTCCGTCAGC CAGTTTAGTC TGACCATCTC ATCTGTAACA TCATTGGCAA CGCTACCTTT     1740
GCCATGTTTC AGAAACAACT CTGGCGCATC GGGCTTCCCA TACAATCGAT AGATTGTCGC     1800
ACCTGATTGC CCGACATTAT CGCGAGCCCA TTTATACCCA TATAAATCAG CATCCATGTT     1860
GGAATTTAAT CGCGGCCTCG AGCAAGACGT TTCCCGTTGA ATATGGCTCA TAACACCCCT     1920
TGTATTACTG TTTATGTAAG CAGACAGTTT TATTGTTCAT GACCAAAATC CCTTAACGTG     1980
AGTTTTCGTT CCACTGAGCG TCAGACCCCG TAGAAAAGAT CAAAGGATCT TCTTGAGATC     2040
CTTTTTTTCT GCGCGTAATC TGCTGCTTGC AAACAAAAAA ACCACCGCTA CCAGCGGTGG     2100
TTTGTTTGCC GGATCAAGAG CTACCAACTC TTTTTCCGAA GGTAACTGGC TTCAGCAGAG     2160
CGCAGATACC AAATACTGTC CTTCTAGTGT AGCCGTAGTT AGGCCACCAC TTCAAGAACT     2220
CTGTAGCACC GCCTACATAC CTCGCTCTGC TAATCCTGTT ACCAGTGGCT GCTGCCAGTG     2280
GCGATAAGTC GTGTCTTACC GGGTTGGACT CAAGACGATA GTTACCGGAT AAGGCGCAGC     2340
GGTCGGGCTG AACGGGGGGT TCGTGCACAC AGCCCAGCTT GGAGCGAACG ACCTACACCG     2400
AACTGAGATA CCTACAGCGT GAGCTATGAG AAAGCGCCAC GCTTCCCGAA GGGAGAAAGG     2460
CGGACAGGTA TCCGGTAAGC GGCAGGGTCG GAACAGGAGA GCGCACGAGG GAGCTTCCAG     2520
GGGGAAACGC CTGGTATCTT TATAGTCCTG TCGGGTTTCG CCACCTCTGA CTTGAGCGTC     2580
GATTTTTGTG ATGCTCGTCA GGGGGGCGGA GCCTATGGAA AAACGCCAGC AACGCGGCCT     2640
TTTTACGGTT CCTGGCCTTT TGCTGGCCTT TTGCTCACAT GTTCTTTCCT GCGTTATCCC     2700
```

-continued

```
CTGATTCTGT GGATAACCGT ATTACCGCCT TTGAGTGAGC TGATACCGCT CGCCGCAGCC    2760

GAACGACCGA GCGCAGCGAG TCAGTGAGCG AGGAAGCGGA AGAGCGCCTG ATGCGGTATT    2820

TTCTCCTTAC GCATCTGTGC GGTATTTCAC ACCGCATATA TGGTGCACTC TCAGTACAAT    2880

CTGCTCTGAT GCCGCATAGT TAAGCCAGTA TACACTCCGC TATCGCTACG TGACTGGGTC    2940

ATGGCTGCGC CCCGACACCC GCCAACACCC GCTGACGCGC CCTGACGGGC TTGTCTGCTC    3000

CCGGCATCCG CTTACAGACA AGCTGTGACC GTCTCCGGGA GCTGCATGTG TCAGAGGTTT    3060

TCACCGTCAT CACCGAAACG CGCGAGGCAG CTGCGGTAAA GCTCATCAGC GTGGTCGTGA    3120

AGCGATTCAC AGATGTCTGC CTGTTCATCC GCGTCCAGCT CGTTGAGTTT CTCCAGAAGC    3180

GTTAATGTCT GGCTTCTGAT AAAGCGGGCC ATGTTAAGGG CGGTTTTTTC CTGTTTGGTC    3240

ACTGATGCCT CCGTGTAAGG GGGATTTCTG TTCATGGGGG TAATGATACC GATGAAACGA    3300

GAGAGGATGC TCACGATACG GGTTACTGAT GATGAACATG CCCGGTTACT GGAACGTTGT    3360

GAGGGTAAAC AACTGGCGGT ATGGATGCGG CGGGACCAGA GAAAAATCAC TCAGGGTCAA    3420

TGCCAGCGCT TCGTTAATAC AGATGTAGGT GTTCCACAGG GTAGCCAGCA GCATCCTGCG    3480

ATGCAGATCC GGAACATAAT GGTGCAGGGC GCTGACTTCC GCGTTTCCAG ACTTTACGAA    3540

ACACGGAAAC CGAAGACCAT TCATGTTGTT GCTCAGGTCG CAGACGTTTT GCAGCAGCAG    3600

TCGCTTCACG TTCGCTCGCG TATCGGTGAT TCATTCTGCT AACCAGTAAG GCAACCCCGC    3660

CAGCCTAGCC GGGTCCTCAA CGACAGGAGC ACGATCATGC GCACCCGTGG CCAGGACCCA    3720

ACGCTGCCCG AGATGCGCCG CGTGCGGCTG CTGGAGATGG CGGACGCGAT GGATATGTTC    3780

TGCCAAGGGT TGGTTTGCGC ATTCACAGTT CTCCGCAAGA ATTGATTGGC TCCAATTCTT    3840

GGAGTGGTGA ATCCGTTAGC GAGGTGCCGC CGGCTTCCAT TCAGGTCGAG GTGGCCCGGC    3900

TCCATGCACC GCGACGCAAC GCGGGGAGGC AGACAAGGTA TAGGGCGGCG CCTACAATCC    3960

ATGCCAACCC GTTCCATGTG CTCGCCGAGG CGGCATAAAT CGCCGTGACG ATCAGCGGTC    4020

CAGTGATCGA AGTTAGGCTG GTAAGAGCCG CGAGCGATCC TTGAAGCTGT CCCTGATGGT    4080

CGTCATCTAC CTGCCTGGAC AGCATGGCCT GCAACGCGGG CATCCCGATG CCGCCGGAAG    4140

CGAGAAGAAT CATAATGGGG AAGGCCATCC AGCCTCGCGT CGCGAACGCC AGCAAGACGT    4200

AGCCCAGCGC GTCGGCCGCC ATGCCGGCGA TAATGGCCTG CTTCTCGCCG AAACGTTTGG    4260

TGGCGGGACC AGTGACGAAG GCTTGAGCGA GGGCGTGCAA GATTCCGAAT ACCGCAAGCG    4320

ACAGGCCGAT CATCGTCGCG CTCCAGCGAA AGCGGTCCTC GCCGAAAATG ACCCAGAGCG    4380

CTGCCGGCAC CTGTCCTACG AGTTGCATGA TAAAGAAGAC AGTCATAAGT GCGGCGACGA    4440

TAGTCATGCC CCGCGCCCAC CGGAAGGAGC TGACTGGGTT GAAGGCTCTC AAGGGCATCG    4500

GTCGAGATCC CGGTGCCTAA TGAGTGAGCT AACTTACATT AATTGCGTTG CGCTCACTGC    4560

CCGCTTTCCA GTCGGGAAAC CTGTCGTGCC AGCTGCATTA ATGAATCGGC CAACGCGCGG    4620

GGAGAGGCGG TTTGCGTATT GGGCGCCAGG GTGGTTTTTC TTTTCACCAG TGAGACGGGC    4680

AACAGCTGAT TGCCCTTCAC CGCCTGGCCC TGAGAGAGTT GCAGCAAGCG GTCCACGCTG    4740

GTTTGCCCCA GCAGGCGAAA ATCCTGTTTG ATGGTGGTTA ACGGCGGGAT ATAACATGAG    4800

CTGTCTTCGG TATCGTCGTA TCCCACTACC GAGATATCCG CACCAACGCG CAGCCCGGAC    4860

TCGGTAATGG CGCGCATTGC GCCCAGCGCC ATCTGATCGT TGGCAACCAG CATCGCAGTG    4920

GGAACGATGC CCTCATTCAG CATTTGCATG GTTTGTTGAA AACCGGACAT GGCACTCCAG    4980

TCGCCTTCCC GTTCCGCTAT CGGCTGAATT TGATTGCGAG TGAGATATTT ATGCCAGCCA    5040

GCCAGACGCA GACGCGCCGA GACAGAACTT AATGGGCCCG CTAACAGCGC GATTTGCTGG    5100
```

```
TGACCCAATG CGACCAGATG CTCCACGCCC AGTCGCGTAC CGTCTTCATG GGAGAAAATA    5160

ATACTGTTGA TGGGTGTCTG GTCAGAGACA TCAAGAAATA ACGCCGGAAC ATTAGTGCAG    5220

GCAGCTTCCA CAGCAATGGC ATCCTGGTCA TCCAGCGGAT AGTTAATGAT CAGCCCACTG    5280

ACGCGTTGCG CGAGAAGATT GTGCACCGCC GCTTTACAGG CTTCGACGCC GCTTCGTTCT    5340

ACCATCGACA CCACCACGCT GGCACCCAGT TGATCGGCGC GAGATTTAAT CGCCGCGACA    5400

ATTTGCGACG GCGCGTGCAG GGCCAGACTG GAGGTGGCAA CGCCAATCAG CAACGACTGT    5460

TTGCCCGCCA GTTGTTGTGC CACGCGGTTG GGAATGTAAT TCAGCTCCGC CATCGCCGCT    5520

TCCACTTTTT CCCGCGTTTT CGCAGAAACG TGGCTGGCCT GGTTCACCAC GCGGGAAACG    5580

GTCTGATAAG AGACACCGGC ATACTCTGCG ACATCGTATA ACGTTACTGG TTTCACATTC    5640

ACCACCCTGA ATTGACTCTC TTCCGGGCGC TATCATGCCA TACCGCGAAA GGTTTTGCGC    5700

CATTCGATGG TGTCCGGGAT CTCGACGCTC TCCCTTATGC GACTCCTGCA TTAGGAAGCA    5760

GCCCAGTAGT AGGTTGAGGC CGTTGAGCAC CGCCGCCGCA AGGAATGGTG CATGCAAGGA    5820

GATGGCGCCC AACAGTCCCC CGGCCACGGG GCCTGCCACC ATACCCACGC CGAAACAAGC    5880

GCTCATGAGC CCGAAGTGGC GAGCCCGATC TTCCCCATCG GTGATGTCGG CGATATAGGC    5940

GCCAGCAACC GCACCTGTGG CGCCGGTGAT GCCGGCCACG ATGCGTCCGG CGTAGAGGAT    6000

CGAGATCCAT ATGACGTCGA CGCGTCTGCA GAAGCTTGCA TGCCAGCTTC TGGTTCGTCG    6060

GCTGGGTGAT GGCGTCGGTT TTGGCCGGCG GCGTCGGCGC GATCGCCAGC GCGAAGCAAC    6120

TGGCGTTCCT CGGCGAACAT AGCGGCATGG TGGCCTTCGG CTTCTTCCGC GACCAGGTGA    6180

AGGACATGCA CTGCGATGCG GACGTGATCC TGGCCCGGTG GGATGAAAAG GCGAACTCGC    6240

CGGTGGTCTA CCGCTGCCCG AAGGCGTACC TGCTCAACAG GTTCGCATCC GCGCCCTTCG    6300

TGCCCTGGCC GGACTACACC GAGGGGGAAA GCGAGGATCT AGGTAGGGCG CTCGCAGCGG    6360

CCCTGCGGGA CGCGAAAAGG TGAGAAAAGC CGGGCACTGC CCGGCTTTAT TTTTGCTGCT    6420

GCGCGTTCCA GGCCGCCCAC ACTCGTTTGA CCTGGCTCGG GCTGCATCCG ACCAGCTTGG    6480

CCGTCTTGGC AATGCTCGAT CCGCCGGAGC GAAGCGTGAT GATGCGGTCG TGCATGCCGG    6540

CGTCACGTTT GCGGCCGGTG TAGCGGCCGG CGGCCTTCGC CAACTGGACA CCCTGACGTT    6600

GACGCTCGCG CCGATCCTCG TAGTCGTCGC GGGCCATCTG CAAGGCGAGC TTCAAAAGCA    6660

TGTCCTGGAC GGATTCCAGA ACGATTTTCG CCACTCCGTT CGCCTCGGCG GCCAGCTCCG    6720

ACAGGTCCAC CACGCCAGGC ACGGCCAGCT TGGCCCCTTT GGCCCGGATC GACGCAACCA    6780

GGCGCTCGGC CTCGGCCAAC GGCAAGCGGC TGATGCGGTC GATCTTCTCC GCAACGACGA    6840

CTTCACCAGG TTGCAGGTCC GCGATCATGC GCAGCAGCTC GGGCCGGTCG GCGCGTGCGC    6900

CGGACGCCTT CTCGCGGTAG ATGCCGGCGA CGTAGTACCC GGCGGCCCGC GTGGCCGCTA    6960

CAAGGCTCTC CTGGCGTTCA AGATTCTGCT CGTCCGTACT GGCGCGCAGG TAGATGCGGG    7020

CGACCTTCAA CCTTCGTCCC TCCGGTTGTT GCTCTCGCGT CGCCATTTCC ACGGCTCGAC    7080

GGCGTGCGGA TCGGACCAGA GGCCGACGCG CTTGCCTCGC GCCTCCTGTT CGAGCCGCAG    7140

CATTTCAGGG TCGGCCGCGC GGCCGTGGAA GCGATAGGCC CACGCCATGC CCTGGTGAAC    7200

CATCGCGGCG TTGACGTTGC GCGGCTGCGG CGGCCGGCTG GCCAGCTCCA TGTTGACCCA    7260

CACGGTGCCC AGCGTGCGGC CGTAACGGTC GGTGTCCTTC TCGTCGACCA GGACGTGCCG    7320

GCGGAACACC ATGCCGGCCA GCGCCTGGCG CGCACGTTCG CCGAAGGCTT GCCGCTTTTC    7380

CGGCGCGTCA ATGTCCACCA GGCGCACGCG CACCGGCTGC TTGTCTACCA GCACGTCGAT    7440
```

```
GGTGTCGCCG TCGATGATGC GCACGACCTC GCCGCGCAGC TCGGCCCATG CCGGCGAGGC      7500

AACGACCAGG ACGGCCAGCG CGGCAGCGGC GCGCAGCATG GCGTAGCTTC GGCGCTTCAT      7560

GCGTGGCCCC ATTGCTGATG ATCGGGGTAC GCCAGGTGCA GCACTGCATC GAAATTGGCC      7620

TTGCAGTAGC CGTCCAGCGC CACCCGCGAG CCGAACGCCG GCGAAAGGTA CTCGACCAGG      7680

CCGGGCCGGT CGCGGACCTC GCGCCCCAGG ACGTGGATGC GCCGGCCGCG TGTGCCGTCG      7740

GGTCCAGGCA CGAAGGCCAG CGCCTCGATG TTGAAGTCGA TGGATAGAAG TTGTCGGTAG      7800

TGCTTGGCCG CCCTCATCGC GTCCCCCTTG GTCAAATTGG GTATACCCAT TTGGGCCTAG      7860

TCTAGCCGGC ATGGCGCATT ACAGCAATAC GCAATTTAAA TGCGCCTAGC GCATTTTCCC      7920

GACCTTAATG CGCCTCGCGC TGTAGCCTCA CGCCCACATA TGTGCTAATG TGGTTACGTG      7980

TATTTTATGG AGGTTATCCA ATGAGCCGCC TGACAATCGA CATGACGGAC CAGCAGCACC      8040

AGAGCCTGAA AGCCCTGGCC GCCTTGCAGG GCAAGACCAT TAAGCAATAC GCCCTCGAAC      8100

GTCTGTTCCC CGGTGACGCT GATGCCGATC AGGCATGGCA GGAACTGAAA ACCATGCTGG      8160

GGAACCGCAT CAACGATGGG CTTGCCGGCA AGGTGTCCAC CAAGAGCGTC GGCGAAATTC      8220

TTGATGAAGA ACTCAGCGGG GATCGCGCTT GACGGCCTAC ATCCTCACGG CTGAGGCCGA      8280

AGCCGATCTA CGCGGCATCA TCCGCTACAC GCGCCGGGAG TGGGGCGCGG CGCAGGTGCG      8340

CCGCTATATC GCTAAGCTGG AACAGGGCAT AGCCAGGCTT GCCGCCGGCG AAGGCCCGTT      8400

TAAGGACATG AGCGAACTCT TTCCCGCGCT GCGGATGGCC CGCTGCGAAC ACCACTACGT      8460

TTTTTGCCTG CCGCGTGCGG GCGAACCCGC GTTGGTCGTC G                         8501
```

(2) INFORMATION FOR SEQ ID NO:2:

(i) SEQUENCE CHARACTERISTICS:
        (A) LENGTH: 12 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:2:

```
Ala Gly Gly Glu Ile Thr Thr Phe Thr Ala Leu Thr
1               5                   10
```

METHOD FOR THE PRODUCTION OF RECOMBINANT PROTEINS, PLASMIDS AND MODIFIED CELLS

This application is a 371 of International Application PCT/FR95/01178, filed Sep. 14, 1995, and which designated the United States.

The present invention relates to the production of recombinant proteins in bacteria. It relates, more specifically, to a novel method which allows an elevated production of recombinant proteins in bacteria and which makes use of an expression system which is particularly stable and efficient and which comprises a bacteriophage T7 promoter and a stabilizing region. The present invention also relates to the plasmids which can be employed in this method and to the recombinant proteins which are produced in this way.

Bacteria, in particular *E. coli*, can be used to produce proteins of varied origin, both from procaryotes and from eucaryotes. In particular, human proteins can be produced in *E. coli*. In order to do this, the structural gene, or the cDNA of the gene which encodes the protein in question, must be placed downstream of the appropriate expression signals (promoter and ribosome attachment site) which are recognized by the *E. coli* expression machinery. The most efficient system used in *E. coli* is that described by Studier (Studier et al., 1990). This system involves using a phage T7 promoter which is specifically recognized by the RNA polymerase of this same bacteriophage (*E. coli* does not, per se, possess any promoter which is recognized by this particular polymerase). This expression system involves induction, for example with IPTG, of the expression of the gene of the phage T7 RNA polymerase (with the latter being placed under the control of an inducible promoter such as PlacUV5 of *E. coli*). This induction results in expression of the gene which is placed under the control of the bacteriophage T7 promoter, which is recognized by the polymerase. Since the polymerase only recognizes the promoter which is upstream of the gene to be expressed, the latter gene is, in general, expressed at a very high level (above a few per cent of the total bacterial protein). A very large number of publications now provide instances of the use of this system which was initially described by Studier (Studier et al., 1990).

As indicated above, bacteria, in particular *E. coli*, are used to produce human proteins of pharmaceutical interest. If the said proteins are then to be used in various therapies, it is advisable for them to be prepared in accordance with the rules of Good Production Practice (GPP). In order to do this, it is essential to have available a production system which is reproducible and which ensures that a product is obtained which is of highly defined quality and very high purity. One of the important features of a method for producing a protein of pharmaceutical interest is the strain which is used to produce the said protein. Thus, it is necessary for this strain to be such as to ensure that the mode of production is reproducible both qualitatively and quantitatively.

At the qualitative level, for example, it is appropriate to produce a protein which is totally homogeneous, that is to say which has a primary sequence which is identical to that of the natural protein. Thus, if a point mutation, which modifies the encoded sequence of the protein to be expressed, were to be produced in a bacterial cell during the course of the fermentation, this would result in the production of a modified protein which was mixed together with the protein having the native sequence. On administration to humans, this modified protein could give rise to an immune reaction which could be very harmful to the treatment or else, in a subsequent treatment, result on this occasion in a severe immune reaction.

At the quantitative level, it is an accepted fact that a method must be reproducible. This constitutes evidence of the quality of the product which is obtained. Thus, in different production batches, the amounts of the protein in question which are synthesized per unit of biomass should be the same, for the same unit of time and using the same culture and growth conditions. A very important feature of this reproducibility of the production of the protein is the presence of the plasmid carrying the expression cassette in the bacterial cells. A fermentation method is even more under control when all the cells still harbour the plasmid at the end of the culture (before and after producing the protein). An antibiotic which selects for the presence of the plasmid is generally added to the culture medium in order to maintain the plasmid in the bacteria. This can pose a variety of problems: the cost of the antibiotic for preparing the fermentation medium; since the antibiotic cannot be sterilized by autoclaving, it is advisable to add it to the culture medium immediately prior to use; the antibiotic may not be stable and may generate transformation products which are toxic in humans or which at least lead, in certain patients, to undesirable side effects; the antibiotic may also, by itself, be toxic in humans or at least lead, in certain patients, to undesirable side effects. In the latter two cases, it will be necessary to demonstrate that the traces of toxic products, corresponding either to the antibiotic or to products derived from it, which are present in the purified product, are lower, on the basis of the doses which are to be administered, than levels which are capable of giving rise to side or toxic effects. This entails elaborate and costly studies.

The present invention solves these problems. Thus, the present invention provides a particularly efficient expression system in which there is no need for an antibiotic to be present in order to maintain the plasmid as the bacterial generations succeed each other in the fermenter. The present invention relates, in particular, to the construction of a plasmid expression system in which expression is effected by means of a bacteriophage T7 promoter and which furthermore includes a stabilizing region. The system according to the invention is particularly advantageous since, contrary to that which is observed in the case of the system of Studier et al., it enables plasmids to be maintained in all the bacterial cells after expression of the protein to be expressed has been induced and in cultural conditions in which there is no antibiotic, that is without any selection pressure. Following induction of expression, the Studier (Studier et al., 1990) plasmids are only present in a very small fraction of the cells. It is evident that the system of the invention has a powerful stabilizing effect on plasmids, thereby increasing the levels at which recombinant proteins are produced and increasing the reproducibility of the method. More specifically, the stabilizing region which is used for constructing the plasmids according to the invention is derived from the par fragment of the plasmid RP4.

The invention primarily relates to an expression plasmid which encompasses a nucleic acid sequence of interest under the control of a bacteriophage T7 promoter and a stabilizing region which comprises all or part of the par region of the plasmid RP4 or of a derivative of this region.

Preferably, the bacteriophage T7 promoter which is used in the plasmids of the present invention is the promoter for the 10 gene.

As indicated above, the stabilizing region which is used in the plasmids of the invention is derived from the par fragment of plasmid RP4 (Gerlitz et al., 1990). This fragment carries a variety of functions (in particular 5 genes designated parA, parB, parC, parD and parE) and, in particular, a protein apparently having a site-specific recombinase activity which probably enables it to resolve plasmid dimers (Eberl et al., 1994). This par fragment can be isolated from plasmid RP4 and cloned into the expression plasmids of the present invention, as described in the examples. Furthermore, this fragment can be modified prior to or following its introduction into the plasmids of the invention. Thus, the stabilizing region of the plasmids of the invention can consist of all or part of the par region of plasmid RP4 or of a derivative of this region.

In particular, the stabilizing region of the plasmids can consist of the PstI insert from the plasmid pTUG3 or of the subfragments SphI-SphI-SphI from pOH23 or SphI-SphI-ClaI from pOH41 or SphI-SphI-BamHII from pGMA28 or SphI-SphI-BamHI from pGMA27, which are described by Gerlitz et al., 1990, or of any subfragment of the PstI insert from pTUG3 which contains at least the SphI-SphI-BamHI insert from pGMA27. While the PstI insert of pTUG3 contains the parCBA-parDE genes and the flanking regions, the inserts of pGMA27 or pGMA28 only contain the parCBA-parDE' genes and the 5' flanking region. The stabilizing region can also consist of the parDE genes or of the parD gene and of its promoter region or of another promoter as has already been described by Roberts et al., 1994. This region can be obtained from the StyI-ClaI fragment which is contained in plasmid pTUG3. The stabilizing region can also consist of any combination of two, three or four par genes contained in plasmid pTUG3, for example parA-parD or parB-parD or parAC-parD or parBA-parDE either with their own promoter region or with another promoter.

The term derivative of the par region includes any fragment which is obtained by genetic and/or chemical modification of the par region and which is capable of achieving stable plasmids according to the invention. In particular, these derivatives can be obtained by means of deletions, mutations, additions, cleavages, ligations, etc. within the par region of plasmid RP4, carried out in accordance with the techniques known to the person skilled in the art. Subsequently, the functional efficiency of the derivatives can be tested as described in the examples (see Example 2, in particular).

Advantageously, the stabilizing region in the plasmids according to the present invention comprises part of the Par region of plasmid RP4. In one particular embodiment, the stabilizing region consists of the fragment contained between residues 6038 and 8499 of the sequence SEQ ID NO:1.

In a preferred embodiment, the plasmids of the invention additionally include the lacO operator and the lacI$^q$ gene. Thus, it has been observed that, despite the presence of a bacteriophage T7 promoter which is specific for a polymerase which is not present in *E. coli*, basal expression of the nucleic acid sequence of interest takes place without inducer. This residual expression can induce some decline in the stability of the plasmid. The presence of the lacO operator and the lacI$^q$ gene in the plasmids of the invention makes it possible advantageously to obtain an expression of the nucleic acid sequence which is more regulated and, in particular, to inhibit any expression in the absence of inducer. The plasmids which incorporate these elements therefore exhibit greater stability and greater control of expression. In order to achieve the desired effect, the lacO operator is advantageously located downstream of the bacteriophage T7 promoter and upstream of the nucleic acid sequence of interest, as indicated in the examples. The lacI$^q$ gene is inserted into the plasmid, preferably together with its own promoter, in a region which is not essential for the desired properties of the plasmid. Thus, the gene is preferably inserted outside the par region and the expression cassette of the nucleic acid sequence of interest. The sequences of this operator and of the lacI$^q$ gene are given in the SEQ ID NO:1 sequence. It is understood that, these elements can be replaced by sequences which are homologous or which possess equivalent functions.

In a particularly preferred embodiment, the plasmids according to the invention also include a transcription terminator which is situated downstream of the nucleic acid sequence of interest. Advantageously, the transcription terminator which is used is that of the bacteriophage T7 gene whose promoter is used. Preferably, the transcription terminator is the T4 terminator of bacteriophage T7.

The nucleic acid sequence of interest which is present in the plasmids according to the invention can be any sequence which encodes a protein which is of pharmaceutical or agrifood interest or which can be used for biocatalysis. The sequence can be a structural gene, a complementary DNA sequence, a synthetic or semi-synthetic sequence, etc.

Preferably, the nucleic acid sequence encodes a protein of pharmaceutical interest which is selected, for example, from among enzymes, blood products, hormones, lymphokines (interleukins, interferons, TNF, etc.), growth factors, neurotransmitters or their precursors or enzymes for synthesizing them, trophic factors: BDNF, CNTF, NGF, IGF, GMF, aFGF, bFGF, NT3, NT5, HARP/pleiotrophin, etc.; apolipoproteins: ApoAI, ApoAIV, ApoE, etc., dystrophin or a minidystrophin, CFTR protein, which is associated with cystic fibrosis, tumour supressor genes: p53, Rb, Rap1A, DCC, k-rev, etc., genes encoding factors involved in coagulation: factors VII, VIII and IX, genes which are involved in DNA repair, etc.

In a particular embodiment of the present invention, the nucleic acid sequence of interest encodes an acidic fibroblast growth factor (aFGF). The cDNA of the native form of the human aFGF gene has been identified, sequenced and cloned (Jaye et al., 1986 and 1987). This cDNA can encode different forms of aFGF depending on the presence of deletions in the N-terminal part, in particular forms encompassing 154, 140 or even 134 amino acids. Furthermore, natural or artificial variants can also be produced, these variants resulting from modifications due to deletion, mutation and/or addition of one or more pairs of bases in the native gene sequence (for example of an N-terminal methionine). In one entirely specific embodiment of the present invention, the nucleic acid sequence of interest encodes aFGF (154). The plasmid pXL2435, which exhibits the sequence SEQ ID NO:1, may be cited as a specific example.

The present invention also relates to a process for producing recombinant proteins. More specifically, the production process according to the invention consists in culturing a bacterium which contains:

a plasmid such as described above which carries a nucleic acid sequence encoding the said protein, and the gene of the bacteriophage T7 RNA polymerase, under conditions which allow expression of the nucleic acid sequence.

As indicated above, the interest of the system resides, in particular, in the use of a bacteriophage T7 promoter which is specifically recognized by the RNA polymerase of the same T7 bacteriophage. The bacterium which is used must therefore harbour, in addition to the plasmid according to the invention, a cassette which allows expression of the bacteriophage T7 RNA polymerase. This cassette can either be integrated into the genome of the bacterium which is employed (*E. coli* strain BL21, DE3), or be carried by a second plasmid or a phage, or else be present on the plasmid of the invention. Advantageously, the gene encoding the bacteriophage T7 RNA polymerase is placed, in the expression cassette, under the control of an inducible promoter such as the lac, trp or recA promoter. This then makes it possible to induce RNA polymerase production in the cell in a controlled manner and, consequently, to control expression of the nucleic acid sequence of interest, which sequence is placed under the control of the promoter which is specific for the said RNA polymerase. Preferably, the inducible promoter which controls expression of the bacteriophage T7 RNA polymerase is the *E. coli* PlacUV5 promoter, which is specifically induced in the presence of IPTG.

As indicated in more detail in the examples, the process of the invention thus makes it possible to produce unmodified proteins at high levels and in a reproducible manner. This process thus makes it possible to produce recombinant proteins of pharmaceutical quality on an industrial scale.

The process according to the present invention is very particularly suitable for producing recombinant fibroblast growth factors (aFGF and bFGF in particular). Thus, the present invention relates, in particular, to a process for preparing recombinant aFGF, according to which process a bacterium which harbours plasmid pXL2435 and the gene of the bacteriophage T7 RNA polymerase is cultured under conditions which permit expression of the nucleic acid sequence, and the aFGF which is produced is recovered.

The present invention will be described in more detail using the examples which follow and which must be regarded as being illustrative and not limiting.

Abbreviations employed:
aFGF: acidic fibroblast growth factor
bp: base pair
OD: optical density
*E. coli*: *Escherichia coli*
IPTG: isopropylthio-β-D-galactoside
kb: kilobases
kDa: kilodaltons
Km: kanamycin
LB: Luria-Bertani medium
PAGE-SDS: electrophoresis using a gel which contains acrylamide, N,N'-methylenebisacrylamide and sodium dodecyl sulphate.
T7: bacteriophage T7

LEGENDS TO THE FIGURES

FIGS. 1A and 1B: Construction of plasmid pXL2435.

A—Construction diagram: The AccI-NdeI fragments of 3.2 kb from pET11a and of 2.8 kb from pXL2283 were ligated to produce plasmid pXL2434; plasmid pXL2434, which had been digested with BqlII, was ligated to the 2.4 kb BamHI fragment from pXL2433 in order to create pXL2435.

B—Map of plasmid pXL2435: aFGF: gene encoding aFGF; Ampr: gene for resistance to ampicillin; Kmr: gene for resistance to kanamycin; lacI$^q$: gene which encodes an elevated synthesis of the Lac repressor; ori: ColE1 origin of replication; parDE'parCBA: genes of the RP4 par locus; pT7: T7 Φ10 promoter and lacO operator; TΦ: T7 TΦ terminator. The arrows indicate the direction in which the genes are transcribed. The restriction enzyme sites which are shown are those which were used for cloning. The numbers in brackets correspond to the positions, in base pairs, on the sequence SEQ ID NO:1.

Figure 2:
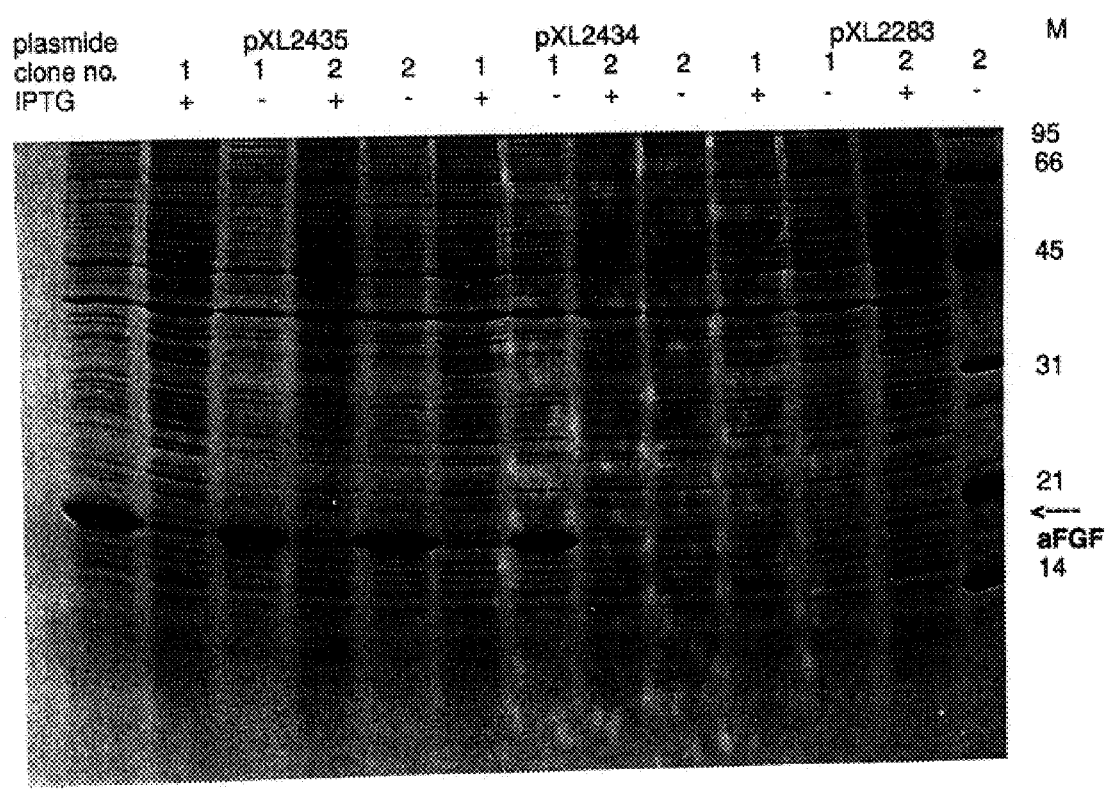

FIG. 2: Depiction of the aFGF protein which is produced by *E. coli* BL21, DE3 in the absence of antibiotic and in the presence of the plasmid pXL2283, pXL2434 or pXL2435 following induction with IPTG. The total cell extracts are loaded on the gel. M: molecular weight marker with molecular weights indicated in kDa; the arrow indicates the molecular weight of the aFGF. Sequence SEQ ID NO:1: Nucleotide sequence of the 8501 bp plasmid pXL2435. Position 1 on the sequence corresponds to the BqlII cleavage site of pET11a. The aFGF gene is situated between positions 108 and 575, and the par locus is situated between positions 6038 and 8499, i.e. parE' from 8248 to 8499, parD from 8001 to 8252, parC from 7850 to 7557, parB from 7560 to 7027 and parA from 7066 to 6407; the T7 TΦ promoter is situated between positions 20 and 36, lacO between positions 39 and 63, the T7 TΦ terminator between positions 586 and 708 and the lacI$^q$ gene between positions 5636 and 4554.

GENERAL CLONING, MOLECULAR BIOLOGICAL AND BIOCHEMICAL TECHNIQUES

The standard molecular biological methods such as centrifugation of plasmid DNA in a caesium chloride/ethidium bromide gradient, restriction enzyme digestion, gel electrophoresis, electroelution of DNA fragments from agarose gels, transformation into *E. coli*, nucleic acid precipitation, etc., are described in the literature (Sambrook et al., 1989). The restriction enzymes were supplied by New-England Biolabs (Biolabs), Bethesda Research Laboratories (BRL) or Amersham Ltd (Amersham).

For the ligations, the DNA fragments are separated according to their size on 0.7% agarose gels, purified by electroelution, extracted with phenol, precipitated with ethanol and then incubated in a 50 mM tris-HCl, pH 7.4, 10 mM MgCl2, 10 mM DTT, 2 mM ATP buffer in the presence of phage T4 DNA ligase (Biolabs). The ligated DNAs or pure plasmid DNAs are used to transform the strain: *E. coli* BL21, DE3 [F$^-$ ompT hsdS$_B$ (r$_B^-$m$_B^-$) qal dcm (DE3)] (Studier et al., 1990) and *E. coli* TG1 [Δ(lac proA,B), supE, thi, hsdD5/F' traD36, proA$^+$, B$^+$, lacI$^q$, lacZΔM15] (Gibson, 1984) which has been rendered competent. The plasmid DNA samples are purified by the alkaline lysis technique described by Sambrook et al., 1989.

The LB culture medium is used for the bacteriological section (Sambrook et al., 1989). Dilutions of the bacterial suspension are then spread on LB medium plates which are supplemented, if necessary, with 50 mg/l kanamycin.

The protocol described by Studier et al., 1990 is used to produce aFGF with the aid of strain BL21, DE3, which harbours a plasmid for expressing aFGF (pXL2283 or pXL2434 or pXL2435, as described in Example 1).

The production of aFGF is measured on total cell extracts. After the bacteria have been lysed, the samples are loaded onto a 15% SDS-PAGE gel which, after electrophoresis, is stained with Coomassie blue (Denefle et al., 1987). The samples derived from strains which are producing aFGF exhibit a band having an apparent molecular weight of 16 kDa. Semi-dry transfer onto a nitrocellulose membrane is carried out (Sambrook et al., 1989) and the membrane is treated in accordance with the protocol accompanying the Vectastain kit (Biosys SA, France) in order to permit calorimetric immunological (anti-bovine aFGF antibody obtained from rabbit and sold by Sigma, France; and anti-rabbit IgG) detection of the aFGF using the avidin/biotinylated peroxidase complex. Another semidry transfer onto a Pro-Blott membrane is carried out (Matsudaira, 1987), the membrane is stained with Coomassie blue and the band of apparent molecular weight of 16 kDa is excised.

This membrane piece is subjected to an Edman, 1956, degradation using a model 477A Applied Biosystems microsequencer which possesses an on-line 120/7 analyser and which is used in accordance with the manufacturer's instructions.

EXAMPLE 1

Construction of a stable and regulated plasmid for expressing the cDNA of human aFGF.

This example describes the constructions which were carried out in order to obtain a stable and highly regulated plasmid for producing aFGF in E. coli.

The cDNA of the native form of the human aFGF gene (470 bp) (Jaye et al., 1986 and 1987) was identified, sequenced and cloned into the expression vector pET9 (Studier et al., 1990) at the NdeI and BamHI sites in order to produce the expression plasmid pMJ42, which is subsequently designated pXL2283 (see FIG. 1). The 2.8 kb NdeI-AccI insert from plasmid pXL2283 was ligated with the 3.2 kb NdeI-AccI fragment from plasmid pET11a (Studier et al., 1990) in order to create the expression plasmid pXL2434. This plasmid differs from pXL2283 in that it also possesses the lacI$^q$ gene and the lacO operator, which enable the aFGF to be expressed in a more regulated manner. BamHI sites were then introduced at the ends of the 2.46 kb parCBA-parDE' fragment derived from plasmid pGMA28 (Gerlitz et al., 1990). In order to do this, the 2.46 kb SphI-SphI-BamHI fragment from pGMA28 was cloned into plasmid pUC18 (Yanish-Perron et al., 1985), which was digested with SphI-BamHI, in order to produce plasmid pGMA60 (H. Schwab et al., personal communication). The 2.46 kb HindIII-EcoRI fragment from plasmid pGMA60 was then cloned into plasmid pMTL22 (Chambers et al., 1988), which was digested with HindIII and EcoRI, in order to produce pXL2433. The BamHI (parCBA-parDE') insert from plasmid pXL2433 was introduced into the BalII site of plasmid pXL2434 in order to create plasmid pXL2435. A diagram of the constructions, and the map of plasmid pXL2435, are depicted in FIG. 1, and the 8501 bp sequence of plasmid pXL2435 is described (SEQ ID NO:1). While the sequence described in the paper by Gerlitz et al., 1990 is only partial (125 base pairs are to be added at the 3' end), this 3' part of the sequence was verified on plasmids pXL2433 and pXL2435 and on the sequence SEQ ID NO:1. A summary of the characteristics of the three expression plasmids is presented in Table 1.

TABLE 1

Characteristics of the expression plasmids

| Plasmids | pXL2283 or pMJ42 | pXL2434 | pXL2435 |
| --- | --- | --- | --- |
| Size (kb) | 4.8 | 6 | 8.5 |
| Derived from | pBR322 | pBR322 | pBR322 |
| Resistance to | kanamycin | kanamycin | kanamycin |
| promoter pT7 | T7 Φ10 | T7 Φ10 | T7 Φ10 |
| lacO | − | + | + |
| TΦ terminator | T7 TΦ | T7 TΦ | T7 TΦ |
| aFGF cDNA | + | + | + |
| lacI$^q$ | − | + | + |
| parCBA-ParDE' | − | − | + |

EXAMPLE 2

Stability of the expression plasmid while producing aFGF

This example describes the production, in liquid medium, of aFGF from a recombinant E. coli. strain harbouring a plasmid for the expression of aFGF which is T7 polymerase-dependent and which strain is cultured without selection for the plasmid. Following aFGF production, the presence of the plasmid is monitored by means of the resistance of the bacteria to kanamycin, the resistance gene of which is carried by the plasmids described in Example 1. Finally, the aFGF protein which has been produced is characterized by standard biochemical methods.

EXAMPLE 2.1

Stability of the expression plasmid in the absence of conditions for inducing aFGF production.

Plasmids pXL2283, pXL2434 and pXL2435 are introduced, by transformation, into the BL21, DE3 strain (Studier et al., 1990). Two transformants are taken at random from among the transformants which are selected on LB agar medium containing kanamycin and cultured for 16 hours in liquid LB medium in the presence of kanamycin. The culture is diluted 1/100 and cultured in LB medium in the presence of kanamycin until the optical density at 600 nm is between 0.2 and 0.6. The cultures are diluted 1/100 in 10 ml of LB medium and the strains are cultured up to an OD of between 0.17 and 0.6. This dilution and growth of the bacteria, at 37° C., in medium which does not contain antibiotic is repeated six times and corresponds to a total of more than 30 generations, after a period of two days. The bacteria are spread on LB agar. After they have grown, 100 clones are streaked on LB agar and on LB agar containing Km. Table 2 shows the incidence of clones which are resistant to Km after at least 30 generations without selection pressure for the plasmid.

This example demonstrates that the RP4 par fragment stabilizes the plasmid in the absence of selection pressure, even though this stabilization effect is only moderate.

EXAMPLE 2.2

Stability of the expression plasmid under conditions for inducing aFGF production.

The bacteria which have been cultured for at least 30 generations in the absence of antibiotic (as described in Example 2.1) are diluted 1/100 in LB medium and cultured for 12 hours, and then diluted once again 1/100 in LB medium. When the bacteria have grown to an OD of 0.5 to 0.8, 1 mM IPTG is added and the bacteria are cultured for 4 hours in order to produce aFGF, which is measured on the total cell extracts which are loaded onto a 15% SDS-PAGE gel which is stained with Coomassie blue (see FIG. 2). The bacteria are spread on LB agar. After they have grown, 100 clones are streaked on LB agar and LB agar containing kanamycin. Table 2 shows the incidence of clones which are resistant to kanamycin after having produced aFGF in the absence of selection pressure for the plasmid.

This example demonstrates, unambiguously, that the par fragment induces very substantial segregational stability subsequent to aFGF expression employing the phage T7 polymerase-dependent expression system.

TABLE 2

Percentage of clones resistant to kanamycin following growth alone, or growth (at least 30 generations) and then expression, without any selection pressure for the plasmid

| Plasmid pXL | Culture dilution without kanamycin | | Culture expression without kanamycin | | |
|---|---|---|---|---|---|
| | Number of generations | Percentage of clones resistant to Km | Number of generations | Percentage of clones resistant to Km | Production of aFGF |
| 2283 (No. 1) | 30 | 20 | 45 | 0.1 | ε |
| 2283 (No. 2) | 30 | 10 | 45 | 0.2 | ε |
| 2434 (No. 1) | 40 | 100 | 45 | 1 | ++ |
| 2434 (No. 2) | 40 | 99 | 45 | 5 | ++ |
| 2435 (No. 1) | 40 | 100 | 45 | 99 | ++ |
| 2435 (No. 1) | 40 | 100 | 45 | 100 | ++ |

ε: expression of aFGF not detected following staining with Coomassie blue
++: very high expression of aFGF; approximately 10% of the total protein.

EXAMPLE 2.3

Characterization of the aFGF protein which is produced in the presence of the plasmid for expressing aFGF.

When produced under the induction conditions described in Example 2.2, the aFGF protein which is obtained is visualized on a 15% PAGE-SDS gel which is stained with Coomassie blue, see FIG. 2, and migrates with an apparent molecular weight of 16 kDa, in accordance with the reported biochemical findings and the published sequence (Jaye et al., 1986 and 1987). Furthermore, this protein is demonstrated by calorimetric immunological detection using anti-bovine aFGF antibodies. The N-terminal sequence of the protein produced by strain BL21, DE3 pXL2435 was then determined using the total extract, which was purified by PAGE-SDS electrophoresis, as described in the general biochemical techniques. The sequence which was obtained is A-E-G-E-I-T-T-F-T-A-L-T (SEQ ID NO: 2); it is identical to the N-terminal sequence of the native protein (Jaye et al., 1986), and the terminal methionine was cleaved off by the E. coli methionylaminopeptidase, as was discussed by Hirel et al., 1989.

This example demonstrates, therefore, that the protein which is produced using an expression plasmid which is stable in E. coli, as described in Example 2.2, is the aFGF protein and that its N-terminal sequence is not truncated.

REFERENCES

Chambers, S., Prior, S., Barstow, D., and Minton, N. (1988) Gene 68: 139–149.
Denefle P., Kovarik, S., Guiton, J. D., Cartwright, T., and Mayaux, J. -F. (1987) Gene 56: 61–70.
Eberl L., Kristensen C., Givskov M., Grohmann E., Gerlitz M., and Schawb H. (1994) Mol. Microbiol. 12: 131–141.
Edman P. (1956) Acta Chemica Scandinavia 10: 761–768.
Gerlitz et al., (1990) J. Bact. 172: 6194–6203
Gibson T. (1984) Ph.D., University of Cambridge, Cambridge, England.
Hirel P., Schmitter P., Dessen P., and Blanquet S. (1989) Proc. Natl. Acad. Sci. 86: 8247–8251.
Jaye M., Howk R., Burgess W., Ricca G., Chui I., Ravera M., O'Brien S., Modi W., Maciag T., and Drohan W. (1986) Science 233: 541–545.
Jaye M., Burgess W., Shaw A., Drohan W. (1987) J. Biol. Chem. 262: 16612–16617.
Matsudaira P. (1987) J. Biol. Chem. 262: 10035–10038.
Roberts et al. (1994) J. Mol. Bol. 237: 35–51.
Sambrook J., Fritsch, E. F., and Maniatis, T. (1989) Molecular Cloning: a Laboratory Manual 2nd edn. Cold Spring Harbor, N.Y.: Cold Spring Harbor Laboratory Press.
Studier, W. F., Rosenberg, A. H., Dunn, J. J., and Duberndorff, J. W. (1990) Methods Enzymol. 185: 89–60.
Yanisch-Perron, C., Vieira, J., Messing, J. (1985) Gene 33: 1033–119.

What is claimed is:

1. An expression plasmid comprising a nucleic acid sequence encoding a protein of interest under the control of a bacteriophage T7 promoter and a stabilizing region comprising all or part of the par region of the plasmid RP4, or of a derivative of the par region wherein said all or part or derivative of the par region of the plasmid RP4 stabilizes the plasmid such that the plasmid may be maintained in bacterial cells without any selection pressure.

2. A plasmid according to claim 1, wherein the bacteriophage T7 promoter is the promoter of gene 10.

3. A plasmid according to claim 1, wherein the stabilizing region comprises part of the par region of plasmid RP4.

4. A plasmid according to claim 3, wherein the stabilizing region comprises residues 6038 to 8499 of the sequence SEQ ID NO:1.

5. A plasmid according to claim 1, further comprising the lacO operator and the lacI$^q$ gene.

6. A plasmid according to claim 5, wherein the lacO operator is downstream of the bacteriophage T7 promoter and upstream of said nucleic acid.

7. A plasmid according to claim 1, wherein the protein is of pharmaceutical interest, agrifood interest, or to be used in biocatalysis.

8. A plasmid according to claim 7, wherein the protein is selected from the group consisting of enzymes, blood products, hormones, lymphokines, growth factors, neurotransmitter synthesizing enzymes, trophic factors, apolipoproteins, dystrophin, minidystrophin, CFTR protein, tumour suppressors, factors involved in coagulation, or proteins involved in DNA repair.

9. A plasmid according to claim 8, wherein the protein is an acidic fibroblast growth factor (aFGF).

10. A plasmid according to claim 9, wherein the protein encodes aFGF (154).

11. A plasmid pXL2435 comprising SEQ ID NO:1.

12. A process for producing recombinant proteins, said process comprising culturing a bacterium comprising:
    a plasmid according to claim 1, and
    a gene encoding the bacteriophage T7 RNA polymerase, under conditions which allow expression of the nucleic acid sequence.

13. A process according to claim 12, wherein the gene encoding the bacteriophage T7 RNA polymerase is under the control of an inducible promoter.

14. A process according to claims 12, wherein the gene encoding the bacteriophage T7 RNA polymerase is integrated into the genome of the bacterium.

15. A process according to claim 12, wherein the bacterium is an *E. coli* strain.

16. A process according to claim 15, wherein the bacterium is the *E. coli* strain BL21, DE3.

17. A process according to claim 12, wherein said protein is aFGF.

18. A process for preparing recombinant aFGF, said process comprising culturing a bacterium comprising plasmid pXL2435 and a gene encoding the bacteriophage T7 RNA polymerase under conditions which produce said aFGF.

19. A bacterium transformed with a plasmid according to claim 1.

* * * * *